United States Patent [19]

Ueno et al.

[11] Patent Number: 5,453,268

[45] Date of Patent: Sep. 26, 1995

[54] ANTIMICROBIAL AND DEODORANT-FINISHED PRODUCT

[75] Inventors: Kazumitsu Ueno, Takatsuki; Ken Yahara, Amagasaki, both of Japan

[73] Assignee: Shinto Paint Co., Ltd., Amagasaki, Japan

[21] Appl. No.: 181,189

[22] Filed: Jan. 13, 1994

[30] Foreign Application Priority Data

Jan. 26, 1993 [JP] Japan .................................. 5-031236

[51] Int. Cl.$^6$ .......................... A01N 25/08; A01N 25/24; B32B 33/00
[52] U.S. Cl. .................................. 424/76.8; 2/400; 2/239; 2/901; 428/253; 428/254; 428/272; 428/274; 428/907
[58] Field of Search .................... 2/901; 424/76.1, 424/76.8; 428/253, 254, 272, 274, 907

Primary Examiner—James C. Cannon
Attorney, Agent, or Firm—Armstrong, Westerman, Hattori, McLeland & Naughton

[57] ABSTRACT

A water-dispersible, antimicrobial and deodorant-finished product for fabrics comprising fine particles of an antimicrobial Schiff base derivative of an aminoglycoside as the active ingredient and a polyoxy-ethylenepolyalkylsiloxane for improving the resistance to washing.

By using the antimicrobial and deodorant-finished product of the present invention, antimicrobial and deodorant fabrics having higher safety, more excellent antimicrobial and deodorant effects and longer duration of the effects than those of the conventional products can be obtained.

1 Claim, No Drawings

ANTIMICROBIAL AND DEODORANT-FINISHED PRODUCT

The present invention relates to an antimicrobial and deodorant-finished product for textile products having a long-lasting antimicrobial effect, namely, an antimicrobial and deodorant-finished product for socks and underwears made of natural or synthetic fibers.

Two properties which are contrary to each other are required of antimicrobial and deodorant-finished products such as underwears. Namely, they should be harmless to the human bodies while they should not kill useful bacteria on the skin which protect the skin from pathogenic bacteria.

Investigations have heretofore been made for imparting antimicrobial properties to textile products, and proposed methods include one wherein an organic sterilizer such as chlorhexidine, quaternary ammonium salt of an organosilicone or quaternary ammonium compound is applied to and deposited on the surface, one wherein metallic copper is woven in the textile, one wherein metallic silver is vapor-deposited, and one wherein a powdery inorganic sterilizer such as zeolite or apatite containing a silver or copper ion is mixed in the textile.

However, when the organic sterilizer is deposited, the antimicrobial effect lasts only a short period of time; and when silver, copper or the like is kneaded in the fiber, the obtained effect is only slight, since the antimicrobial metal is difficultly ionized and, therefore, the product can be practically used for only a limited purpose disadvantageously.

Although 1-L-(1,3,5/2,4)-1,5-diamino-4-o-(2,6-diamino-2,6-dideoxy-α-D-glucopyranosyl)-2,3- cyclohexanediol is an aminoglycoside highly safe for human bodies and having excellent antimicrobial properties, it has a defect that it is easily dissolved out upon washing, since it is highly soluble in water.

An object of the present invention is to complete an antimicrobial and deodorant-finished product capable of maintaining its antimicrobial properties for a long period of time, having excellent processability, storage stability and high safety for the environment, and harmless to the human bodies by overcoming the problems of the prior art.

After intensive investigations, the inventors have completed an antimicrobial and deodorant-finished product free from the above-described defects by converting 1-L-(1,3,5/2,4)-1,5-diamino-4-o-(2,6-diamino-2,6-dideoxy-α-D-glucopyranosyl)-2,3- cyclohexanediol, which is a highly water-soluble aminoglycoside highly safe for the human bodies used as the antimicrobial component, into a water-insoluble Schiff base derivative of the aminoglycoside by reacting at least one primary amino group of this compound with an aromatic aldehyde, selecting the product having an average particle diameter of 1 μm or below as the antibacterial component so as to obtain an improved resistance to washing, and adding a polyoxyethylenepolyalkylsiloxane as an adherent agent to the product.

The present invention provides an antimicrobial and deodorant-finished product, characterized by comprising a Schiff base derivative of an amino-glycoside obtained by reacting at least one primary amino group of 1-L-(1,8,5/2,4)-1,5-diamino-4-o-(2,6-diamino-2,6-dideoxy-α-D-glucopyranosyl) -2,3cyclohexanediol with an aromatic aldehyde, the derivative having an average particle diameter of 1 μm or below, and a polyxoyethylenepolyalkylsiloxane ($C_1$ to $C_6$).

A water-dispersible formulation of the antimicrobial and deodorant-finished product of the present invention can be easily obtained by further adding thereto a dispersing agent, thickener, etc., by a known technique.

The antimicrobial and deodorant-finished product of the present invention desirably comprises 1 to 40% by weight of the Schiff base derivative of the aminoglycoside as the antimicrobial component and 0.1 to 30% by weight of the polyoxyethylenepolyalkyl-siloxane as the adherent agent. When the concentration is below the lower limit, no expected antimicrobial and deodorant effect can be obtained in an ordinary concentration thereof in the processed products. On the contrary, when it exceeds the upper limit, the stability of the preparation is impaired.

In the present invention 1-L-(1,3,5/2,4)-1,5-diamino-4-o-(2,6-diiamino-2,6-dideoxy-α -D-glucopyranosyl)-2,3-cyclohexanediol is reacted with the aromatic aldehyde in a solvent selected from among lower alcohols such as methanol and ethanol, THF, methyl Cellosolve and mixtures of them with water at ambient temperature. The aromatic aldehydes usable herein include anisaldehyde, salicylaldehyde and terephthalaldehyde.

Although the polyoxyethylenepolyalkylsiloxane to be used in the present invention is preferably linear, it may be partially or wholly branched or crosslinked. The alkyl group has 1 to 6 carbon atoms, and preferred is a methyl group.

The antimicrobial and deodorant-finished product of the present invention can be used for processing textiles by dispersing it in water together with a processing agent such as a softening agent. In processing the fibers, the effective concentration is such that the amount of the Schiff base derivative of the aminoglycoside deposited on the fibers is 5 to 10,000 ppm. When it is below 5 ppm, the antimicrobial effect is insufficient and, on the contrary, when it exceeds 10,000 ppm, useful bacteria on the skin are also killed and pathogenic bacteria resistant to chemicals preferentially propagate on the skin to cause a skin disease or the like. Although the amount of the polyethylenepolyalkylsiloxane deposited on the fibers is not particularly limited, it is preferably 5 to 100 ppm.

When antifugal properties are required, a fungicide such as thiabendazole can be added.

Example 1

55% by weight of 1-L-(1,3,5/2,4)-1,5-diamino-4-o-(2,6-diamino-2,6-dideoxy-α -D-glucopyranosyl)-2,3cyclohexanediol was reacted with 45% by weight of terephthalaldehyde to form the Schiff base derivative of the aminoglycoside (average particle diameter: 0.8 μm). 90 g of an aqueous solution containing 1 g of an anionic dispersing agent, 1 g of polyoxyethylenestyryl phenyl ether and 0.4 g of xanthan gum was dispersed in 10 g of the Schiff base derivative in a sand mill for 45 min. 10 g of an emulsion containing 30 wt. % of polyoxyethylenepolymethylsiloxane was added to the resultant dispersion to obtain the antimicrobial and deodorant-finished product (A) of the present invention.

A 2 wt. % processing solution of the antimicrobial and deodorant-finished product (A) of the present invention was prepared. A bleached cotton fabric was immersed therein, then squeezed with a mangle to obtain a pick-up ratio of 75 wt. % and dried at 130° C. for 2 min to obtain the antimicrobial and deodorant-finished fabric (A-1) according to the present invention.

The same procedure as that described above was repeated except that the Schiff base derivative of the aminoglycoside in the antimicrobial and deodorant-finished product (A) of the present invention was replaced with one having an average particle diameter of 3.0 μm to obtain an antimicrobial and deodorant-finished fabric (H-1) as a control. The fabric (H-1), nonprocessed bleached cotton fabric (C-1) and the antimicrobial and deodorant-finished fabric (A-1) of the present invention were tested according to the standard of Association of Antibacterial Treatment for Textile, Japan, by the colony count method. The method comprises washing the fabrics ten times according to Method 103 of JIS L 0217, inoculating them with *Staphylococcus aureus* as a test bacterium, subtracting the seeding viable count from the viable count after the culture for 18 h to calculate the increment, and subtracting the increment in the processed sample from that in the unprocessed sample to calculate the increment difference. The results are given in Table 1. The antimicrobial and deodorant-finished fabric (A-1) of the present invention had the increment different exceeding 1.6, which is the critical difference as stipulated by the Association, suggesting that the antimicrobial effect of the product (A-1) was far superior to the critical value. Scarcely any difference was found between the antimicrobial and deodorant-finished fabric (H-1) as the control and the nonprocessed fabric, which suggested that no effect could be obtained in the fabric (H-1).

TABLE 1

|  | Smp. No. |  | Viable count | Increment | Increment difference |
|---|---|---|---|---|---|
|  |  | seeding viable count | $6.4 \times 10^5$ log 5.8 | * | * |
| After 18-hour culture | C-1 | unprocessed | $2.1 \times 10^8$ log 8.3 | 2.5 | * |
|  | A-1 | Ex. | $1.0 \times 10^2$ log 2.0 | −3.8 | 5.0 |
|  | H-1 | Comp. Ex. | $1.2 \times 10^8$ log 8.1 | 2.3 | 0.2 |

Example 2

50% by weight of 1-L-(1,3,5/2,4)-1,5-diamino-4-o-(2,6-diamino-2,6-dideoxy-α-D-glucopyranosyl)-2,3cyclohexanediol was reacted with 50% by weight of terephthalaldehyde to form the Schiff base derivative of the aminoglycoside (average particle diameter: 0.8 μm). 90 g of an aqueous solution containing 1g of sodium naphthalenesulfonate, 1 g of modified polysodium acrylate and 0.2 g of hydroxyethylcellulose was dispersed in 10 g of the Schiff base derivative in a sand mill for 45 min. 10 g of an emulsion containing 20 wt. % of polyoxyethylenepolybutylsiloxane was added to the resultant dispersion to obtain the antimicrobial and deodorant-finished product (B) of the present invention.

A 4 wt. % processing solution of the antimicrobial and deodorant-finished product (B) of the present invention was prepared. Men's socks (made of cotton and nylon; not finished by the antimicrobial and deodorant method) on the market were immersed therein, then squeezed with a mangle to obtain a pick-up ratio of 50 wt. %, dried at 110° C. for 20 min and cured at 140° C. for 20 sec to obtain the antimicrobial and deodorant-finished fabric (B-1) according to the present invention.

The following fabrics were washed ten times and then tested by the colony count method according to the standard of Association of Antibacterial Treatment for Textile, Japan: antimicrobial and deodorant-finished fabric (I-1) as a control prepared in the same manner as the one described above except that the polyoxypolybutylsiloxane of the antimicrobial and deodorant-finished product (B) of the present invention was replaced with water; antimicrobial and deodorant-finished fabric (J-1) as another control prepared in the same manner as the one described above except that the polyoxypolybutylsiloxane of the antimicrobial and deodorant-finished product (B) of the present invention was replaced with a urethane emulsion (UE-40-499: trade name of ICI); unprocessed men's socks (C-2); commercially available, antimicrobial and deodorant-finished men's socks (K-1) which were further processed with a quaternary ammonium salt of an organosilicon; and the antimicrobial and deodorant-finished fabric (B-1) of the present invention. The results are given in Table 2. The antimicrobial and deodorant-finished fabric (B-1) of the present invention exhibited excellent antimicrobial properties. Scarcely any difference was found among the antimicrobial and deodorant-finished fabrics (I-1), (J-1) and (K-1) as the control and the nonprocessed fabric (C-2), which suggested that no effect could be obtained in them.

TABLE 2

|  | Smp. No. |  | Viable count | Increment | Increment difference |
|---|---|---|---|---|---|
|  |  | seeding viable count | $2.2 \times 10^5$ log 5.3 | * | * |
| After 18-hour culture | C-2 | unprocessed | $3.0 \times 10^8$ log 8.5 | 3.2 | * |
|  | B-1 | Ex. | $3.2 \times 10^3$ log 3.5 | −1.8 | 5.0 |
|  | I-1 | Comp. Ex. | $8.5 \times 10^7$ log 7.9 | 2.6 | 0.6 |
|  | J-1 | Comp. Ex. | $2.1 \times 10^5$ log 5.3 | 0 | 3.2 |
|  | K-1 | Comp. Ex. | $2.1 \times 10^6$ log 6.3 | 1.0 | 2.2 |

By using the antimicrobial and deodorant-finished product of the present invention, antimicrobial and deodorant fabrics having higher safety, more excellent antimicrobial and deodorant effects and longer duration of the effects than those of the conventional products can be obtained.

We claim:
1. An antimicrobial and deodorant-finished product, characterized by comprising a Schiff base derivative of an aminoglycoside obtained by reacting at least one primary amino group of 1-L-(1,3,5/2,4)-1,5-diamino-4-o-(2,6-diamino-2,6-dideoxy-α -D-glucopyranosyl)-2,3cyclohexanediol with an aromatic aldehyde, the derivative having an average particle diameter of 1 μm or below, and a polyoxyethylenepolyalkylsiloxane ($C_1$ to $C_6$).

* * * * *